United States Patent [19]
Church et al.

[11] Patent Number: 6,045,777
[45] Date of Patent: *Apr. 4, 2000

[54] METHOD FOR ENHANCING THE ECHOGENICITY AND DECREASING THE ATTENUATION OF MICROENCAPSULATED GASES

[75] Inventors: Charles C. Church, Arlington; Howard Bernstein, Cambridge; Julie Ann Straub, Winchester; Henry T. Brush, Somerville, all of Mass.

[73] Assignee: Acusphere, Inc., Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/885,933

[22] Filed: Jun. 30, 1997

[51] Int. Cl.$^7$ .............................. A61K 49/04; A61B 8/14
[52] U.S. Cl. ......................... 424/9.52; 600/458; 600/441
[58] Field of Search ................................. 424/9.52, 9.51, 424/9.5, 450, 489; 600/458, 441

[56] References Cited

U.S. PATENT DOCUMENTS

| | | |
|---|---|---|
| 5,123,414 | 6/1992 | Unger . |
| 5,334,381 | 8/1994 | Unger . |
| 5,352,435 | 10/1994 | Unger . |
| 5,611,344 | 3/1997 | Bernstein et al. . |
| 5,639,473 | 6/1997 | Grinstaff et al. ................ 424/450 |

FOREIGN PATENT DOCUMENTS

| | | |
|---|---|---|
| 0 458 745 A1 | 11/1991 | European Pat. Off. . |
| WO 80/02365 | 11/1980 | WIPO . |
| WO 92/18164 | 10/1992 | WIPO . |
| WO 92/21382 | 12/1992 | WIPO . |
| WO 93/25242 | 12/1993 | WIPO . |
| WO 94/08627 | 4/1994 | WIPO . |
| WO 95/03357 | 2/1995 | WIPO . |
| WO 95/23615 | 9/1995 | WIPO . |
| WO 96/04018 | 2/1996 | WIPO . |
| WO 96/15815 | 5/1996 | WIPO . |
| WO 97/22409 | 6/1997 | WIPO . |

OTHER PUBLICATIONS

Beck, L.R. et al., *Fertil. Steril.*, 31, 545 (1979).
Benita, S. et al., *J. Pharm. Sci.*, 73, 1721 (1984).
Carroll, B.A. et al., *Invest. Radiol.*, vol. 15, pp. 260–266 (1980).
Carroll, B.A. et al., *Radiology*, vol. 143, pp. 747–750 (1982).
Church, C., *J. Acoustical Soc. Amer.*, 97(3):1510–1521 (1995).
Commander, K.W. et al., *J. Acoust. Soc. Amer.*, 85(2): 732–746 (1989).
Feinstein et al., *J. Am. Coll. Cardiol.*, vol. 11, pp. 59–65 (1988).
Fritzsch, T. et al., *Invest. Radiol*, vol. 23 (Suppl 1), pp. 302–305 (1988).
Fritzsch, T. et al., *Invest Radiol.*, vol. 25 (Suppl 1), 160–161 (1990).
Mathiowitz, E. et al.,*J. Scanning Microscopy*, 4, 329 (1990).
Mathiowitz, E. et al., *Reactive Polymers*, 6, 275 (1987).
Ophir, J. and Parker, K.J., Contrast Agents in Diagnostic Ultrasound, Ultrasound in Medicine & Biology, vol. IS, n. 4, p. 319, 323 (1989).
Parker, K.J. and Wagg,R.C., "Measurement of Ultrasonic Attenuation Within Regions selected from B–Scan Images," *IEEE Trans. Biomed. Enar. BME* 30(8), pp. 431–437 (1983).
Parker, K.J., Wagg, R.C. and Lerner, R.M., "Attenuation of Ultrasound Magnitude and Frequency Dependence for Tissue Characterization," *Radiology*, 153(3), pp. 785–788 (1984).
Rovai, D. et al., *J. Am. Coll. Cardiol.*, vol. 10, pp. 125–134 (1987).
Schneider et al.,*Invest. Radiol.*, vol. 27, pp. 134–139 (1992).
Smith, M. et al., *J. Am. Coll. Cardiol.*, vol. 13, pp. 1622–1628 (1989).
Wible, J.H. et al., *J. Am. Soc. Echocardiogr.*, vol. 9, pp. 442–451 (1996).

Primary Examiner—Jose' G. Dees
Assistant Examiner—Michael G. Hartley
Attorney, Agent, or Firm—Arnall Golden & Gregory, LLP

[57] ABSTRACT

It has been discovered microparticles formed from natural or synthetic polymer with thicker walls have significantly enhanced echogenicity as compared with microparticles having thinner walls. The effect of wall thickness has been determined experimentally as well as inserted into a formula for use in predicting the optimum conditions. In the preferred embodiment, the polymers are synthetic biodegradable polymers and the wall thickness is between about 100 and 660 nm, although wall thicknesses from about 20 nm to in excess of 500 nm can be used. The microparticles are manufactured with a diameter suitable for the targeted tissue to be imaged, for example, with a diameter of between 0.5 and 8 microns for intravascular administration, and a diameter of between 0.5 and 5 mm for oral administration for imaging of the gastrointestinal tract or other lumens. Preferred polymers are polyhydroxy acids such as polylactic acid-co-glycolic acid, polylactide or polyglycolide, most preferably conjugated to polyethylene glycol or other materials inhibiting uptake by the reticuloendothelial system (RES). The microspheres may be used in a variety of ultrasound imaging applications including cardiology applications, blood perfusion applications as well as for organ and peripheral vein imaging.

19 Claims, 4 Drawing Sheets

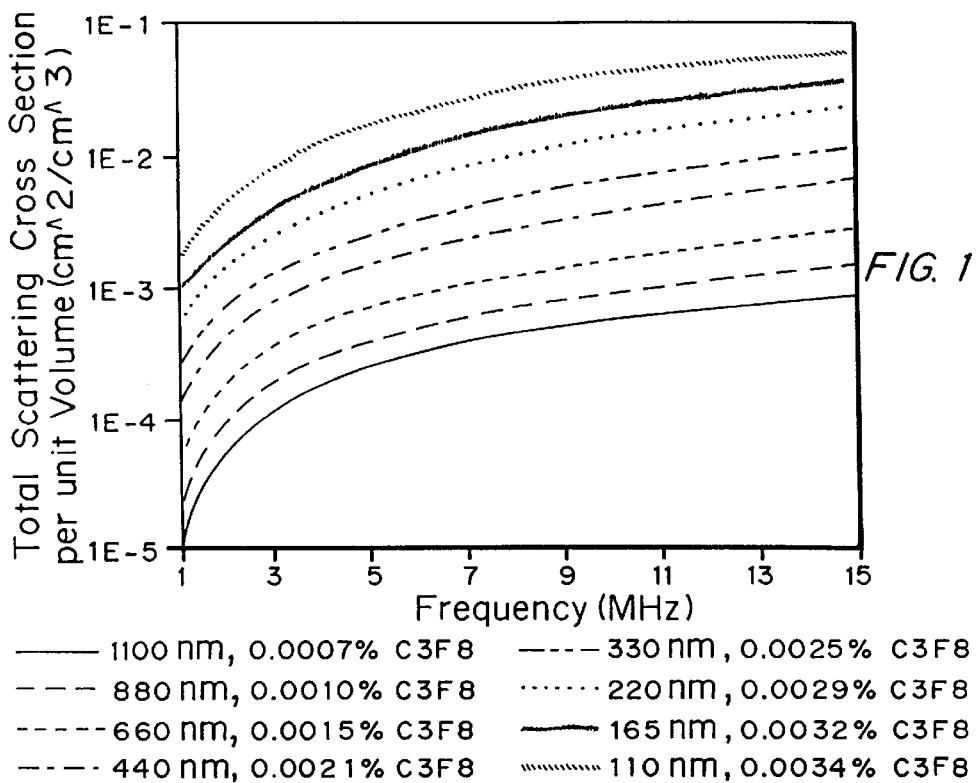
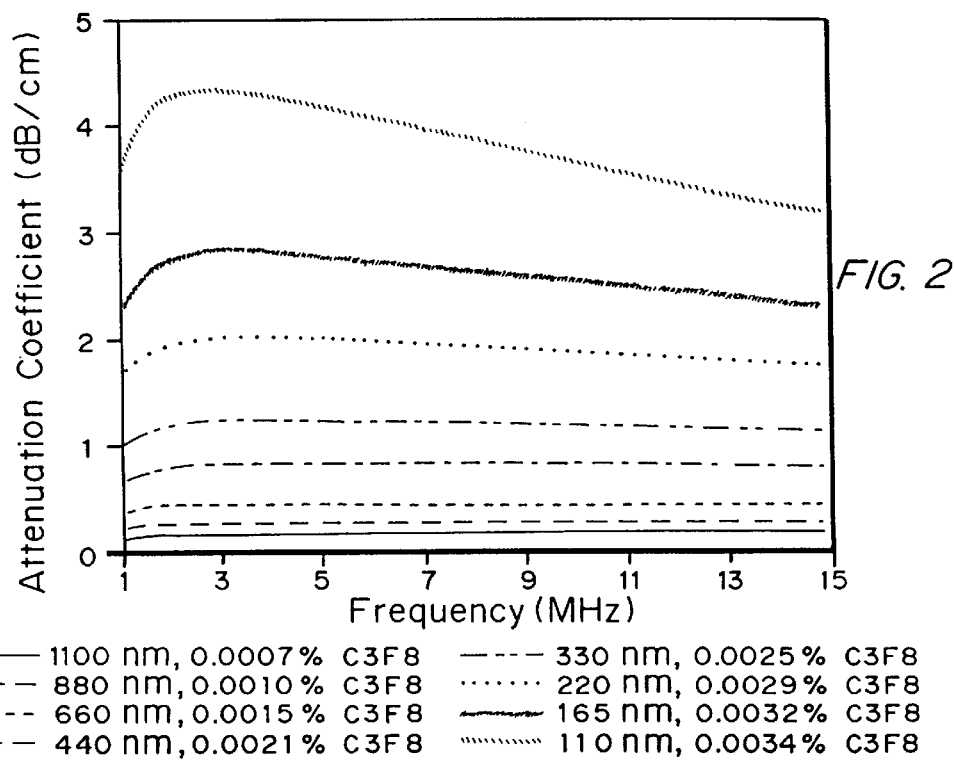

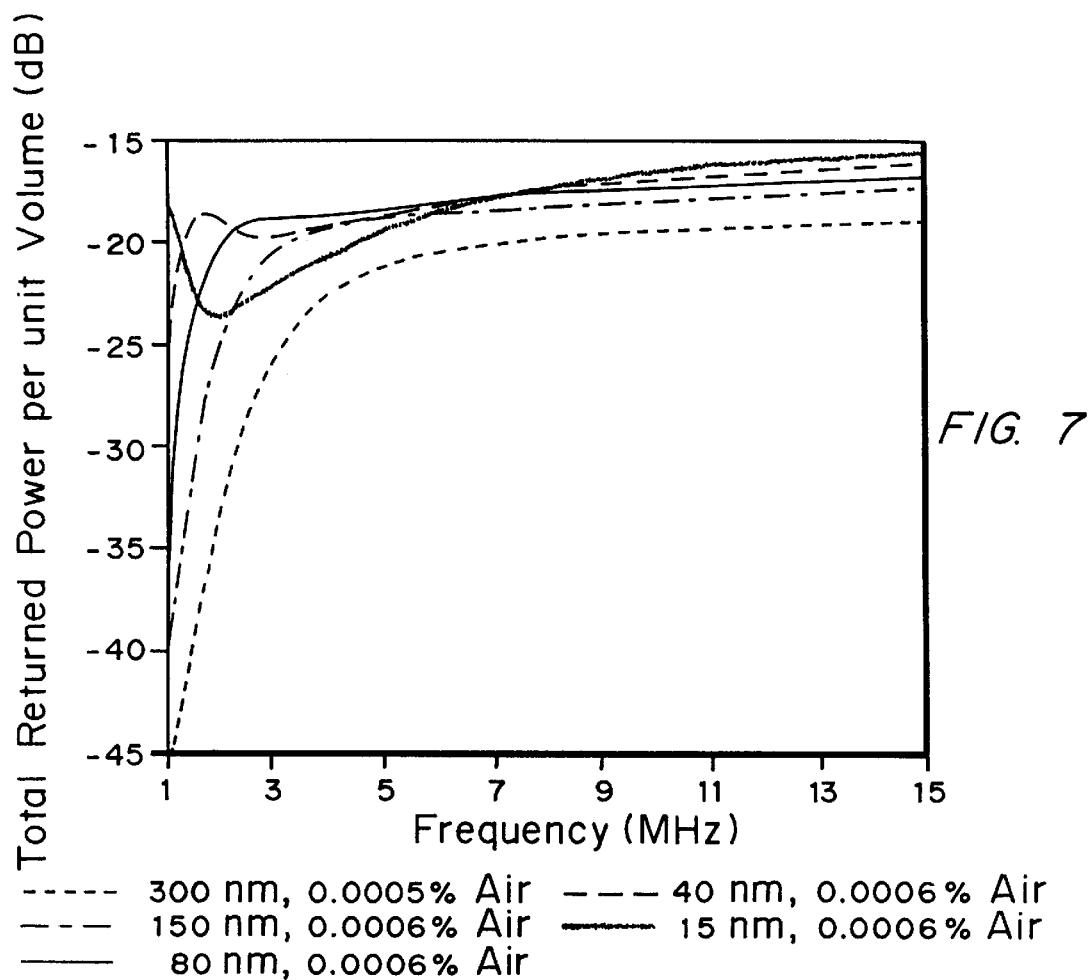

METHOD FOR ENHANCING THE ECHOGENICITY AND DECREASING THE ATTENUATION OF MICROENCAPSULATED GASES

BACKGROUND OF THE INVENTION

The present invention is generally in the area of diagnostic imaging agents, and is particularly directed to microparticulate ultrasound imaging contrast agents having increased echogenicity and decreased attenuation as a function of the thickness of the polymer membrane.

When using ultrasound to obtain an image of the internal organs and structures of a human or animal, ultrasound waves, waves of sound energy at a frequency above that discernable by the human ear, are reflected as they pass through the body. Different types of body tissue reflect the ultrasound waves differently and the reflections that are produced by the ultrasound waves reflecting off different internal structures are detected and converted electronically into a visual display.

For some medical conditions, obtaining a useful image of the organ or structure of interest is especially difficult because the details of the structure are not adequately discernible from the surrounding tissue in an ultrasound image produced by the reflection of ultrasound waves absent a contrast-enhancing agent. Detection and observation of certain physiological and pathological conditions may be substantially improved by enhancing the contrast in an ultrasound image by injecting or infusing an agent into an organ or other structure of interest. In other cases, detection of the movement of the contrast-enhancing agent itself is particularly important. For example, a distinct blood flow pattern that is known to result from particular cardiovascular abnormalities may only be discernible by infusing a contrast-enhancing agent into the bloodstream and observing the dynamics of the blood flow.

Materials that are useful as ultrasound contrast agents operate by having an effect on ultrasound waves as they pass through the body and are reflected to create the image from which a medical diagnosis is made. Different types of substances affect ultrasound waves in different ways and to varying degrees. Moreover, certain of the effects caused by contrast-enhancing agents are more readily measured and observed than others. In selecting an ideal composition for a contrast-enhancing agent, one would prefer the substance that has the most dramatic effect on the ultrasound wave as it passes through the body. Also, the effect on the ultrasound wave should be easily measured. There are two effects which can be seen in an ultrasound image: backscatter and beam attenuation.

BACKSCATTER: When an ultrasound wave that is passing through the body encounters a structure, such as an organ or other body tissue, the structure reflects a portion of the ultrasound wave. Different structures within the body reflect ultrasound energy in different ways and in varying strengths. This reflected energy is detected and used to generate an image of the structures through which the ultrasound wave has passed. The term "backscatter" refers to the phenomenon in which ultrasound energy is scattered back towards the source by a substance with certain physical properties.

It has long been recognized that the contrast observed in an ultrasound image may be enhanced by the presence of substances known to cause a large amount of backscatter. When such a substance is administered to a distinct part of the body, the contrast between the ultrasound image of this part of the body and the surrounding tissues not containing the substance is enhanced. It is well understood that, due to their physical properties, different substances cause backscatter in varying degrees. Accordingly, the search for contrast-enhancing agents has focused on substances that are stable and non-toxic and that exhibit the maximum amount of backscatter.

The capability of a substance to cause backscatter of ultrasound energy depends on characteristics of the substance such as its ability to be compressed. When examining different substances, it is useful to compare one particular measure of the ability of a substance to cause backscatter known as the "scattering cross-section." The scattering cross-section of a particular substance is proportional to the radius of the scatterer, and also depends on the wavelength of the ultrasound energy and on other physical properties of the substance, J. Ophir and K. J. Parker, *Contrast Agents in Diagnostic Ultrasound*, Ultrasound in Medicine & Biology, vol. IS, n. 4, p. 319, 323 (1989).

In evaluating the utility of different substances as ultrasound contrast agents, i.e. gases, liquids, or solids, one can calculate which agents should have the higher scattering cross-section and, accordingly, which agents should provide the greatest contrast in an ultrasound image. It can be assumed that the compressibility of a solid particle is much less than that of the surrounding medium and that the density of the particle is greater. Using this assumption, the scattering cross section of a solid particle contrast-enhancing agent has been estimated as 1.75 (Ophir and Parker, supra, at 325). For a pure liquid scatterer, the adiabatic compressibility and density of the scatterer and the surrounding medium are likely to be approximately equal, which would yield the result that liquids would have a scattering cross-section of zero. However, liquids may exhibit some backscatter if large volumes of a liquid agent are present. For example, if a liquid agent passes from a very small vessel to a very large one such that the liquid occupies substantially all of the vessel, the liquid may exhibit measurable backscatter. Nevertheless, it is appreciated by those skilled in the art that pure liquids are relatively inefficient scatterers.

The scattering cross-section of a gas is substantially different and greater than a liquid or solid, in part, because a gas bubble can be compressed to a much greater degree than a liquid or solid. Moreover, free gas bubbles in a liquid exhibit oscillatory motion such that, at certain frequencies, gas bubbles will resonate at a frequency near that of the ultrasound waves commonly used in medical imaging. As a result, the scattering cross-section of a gas bubble can be over a thousand times larger than its physical size.

BEAM ATTENUATION: Another effect which can be observed from the presence of certain contrast-enhancing agents is the attenuation of the ultrasound wave. The intensity of the ultrasound wave decreases as the wave passes through the volume of tissue or blood containing the contrast agent. The decrease in wave intensity is the result of both ultrasound which is backscattered by the agent as well as dissipation of the wave as it interacts with the contrast agent. If the beam is too attenuated, the power returned to the transducer from regions distal to the contrast agent will be low leading to poor imaging depth. The use of beam attenuation differences in different tissue types has been attempted as an image enhancement method. Image contrast has been observed in conventional imaging due to localized attenuation differences between certain tissue types. K. J. Parker and R. C. Wagg, "Measurement of Ultrasonic Attenuation Within Regions selected from B-Scan Images," *IEEE Trans. Biomed. Enar. BME* 30(8), p. 431–37 (1983); K. J. Parker, R. C. Wagg, and R. M. Lerner, "Attenuation of Ultrasound Magnitude and Frequency Dependence for Tissue Characterization," Radiology, 153(3), p. 785–88 (1984). It has been hypothesized that measurements of the attenuation of a region of tissue taken before and after infusion of an agent may yield an enhanced image. However, techniques based on attenuation contrast as a means to measure the contrast enhancement of a liquid agent are not well-developed and, even if fully developed, may suffer from limitations as to the internal organs or structures with which this technique can be used. For example, it is unlikely that a loss of attenuation due to liquid contrast agents could be observed in the image of the cardiovascular system because of the high volume of liquid contrast agent that would need to be present in a given vessel before a substantial difference in attenuation could be measured.

In summary, diagnostic ultrasound is a powerful, non-invasive tool that can be used to obtain information on the internal organs of the body. The advent of grey scale and color Doppler imaging have greatly advanced the scope and resolution of the technique. Although techniques for carrying out diagnostic ultrasound examinations have improved significantly, as have those for making and using contrast agents, there is still a need to enhance the resolution of the imaging for cardiac perfusion and cardiac chambers, solid organs, renal perfusion, solid organ perfusion, and Doppler signals of blood velocity and flow direction during real-time imaging. The development of ultrasound contrast agents has focused on the use of biocompatible gases, either as free gas bubbles or as gases encapsulated in natural or synthetic shell materials.

A variety of natural and synthetic polymers has been used to encapsulate a gas, such as air, for use as imaging contrast agents. Schneider et al., *Invest. Radiol.*, Vol. 27, pp. 134–139 (1992) describes 3 micron, air-filled polymeric particles. These particles were reported to be stable in plasma and under applied pressure. However, at 2.5 MHz, their echogenicity was low. Another type of encapsulated gas microbubble suspension has been obtained from sonicated albumin. Feinstein et al., *J. Am. Coll. Cardiol.*, Vol. 11, pp. 59–65 (1988). Feinstein describes the preparation of microbubbles that are appropriately sized for transpulmonary passage with excellent stability in vitro. However, these microbubbles are short-lived in vivo, having a half life on the order of a few seconds (which is approximately equal to one circulation pass) because they quickly dissolve in undersaturated liquids, for example blood. Wible, J. H. et al., *J. Am. Soc. Echocardiogr.*, Vol. 9, pp. 442–451 (1996). Gelatin-encapsulated air bubbles have been described by Carroll et al. (Carroll, B. A. et al., *Invest. Radiol.*, Vol. 15, pp. 260–266 (1980), and Carroll, B. A. et al., *Radiology*, Vol. 143, pp. 747–750 (1982)), but due to their large sizes (12 and 80 $\mu$m) they would not be likely to pass through pulmonary capillaries. Gelatin-encapsulated microbubbles have also been described in PCT/US80/00502 by Rasor Associates, Inc. These are formed by "coalescing" the gelatin.

Air microbubbles stabilized by microcrystals of galactose (SHU 454 and SHU 508) have also been reported by Fritzsch, T. et al., *Invest. Radiol.* Vol. 23 (Suppl 1), pp. 302–305 (1988); and Fritzsch, T. et al., *Invest. Radiol.*, Vol. 25 (Suppl 1), 160–161 (1990). The microbubbles last up to 15 minutes in vitro but less than 20 seconds in vivo. Rovai, D. et al., *J. Am. Coll. Cardiol.*, Vol. 10, pp. 125–134 (1987); and Smith, M. et al., *J. Am. Coll. Cardiol.*, Vol. 13, pp. 1622–1628 (1989). Gas microbubbles encapsulated within a shell of a fluorine-containing material are described in WO 96/04018 by Molecular Biosystems, Inc.

European Patent Application No. 90901933.5 by Schering Aktiengesellschaft discloses the preparation and use of microencapsulated gas or volatile liquids for ultrasound imaging, where the microcapsules are formed of synthetic polymers or polysaccharides. European Patent Application No. 91810366.4 by Sintetica S. A. (0 458 745 A1) discloses air or gas microballoons bounded by an interfacially deposited polymer membrane that can be dispersed in an aqueous carrier for injection into a host animal or for oral, rectal, or urethral administration, for therapeutic or diagnostic purposes. WO 92/18164 by Delta Biotechnology Limited describes the preparation of microparticles by spray drying under very controlled conditions as to temperature, rate of spraying, particle size, and drying conditions, of an aqueous protein solution to form hollow spheres having gas entrapped therein, for use in imaging. WO 93/25242 describes the synthesis of microparticles for ultrasonic imaging consisting of a gas contained within a shell of polycyanoacrylate or polyester. WO 92/21382 discloses the fabrication of microparticle contrast agents which include a covalently bonded matrix containing a gas, wherein the matrix is a carbohydrate. U.S. Pat. Nos. 5,334,381, 5,123,414 and 5,352,435 to Unger describe liposomes for use as ultrasound contrast agents, which include gases, gas precursors, such as a pH activated or photo-activated gaseous precursor, as well as other liquid or solid contrast enhancing agents. WO 95/23615 by Nycomed discloses microcapsules for imaging which are formed by coacervation of a solution, for example, a protein solution, containing a perfluorocarbon. PCT/US94/08416 by Massachusetts Institute of Technology discloses microparticles formed of polyethylene glycol-poly(lactide-co-glycolide) block polymers having imaging agents encapsulated therein, including gases such as air and perfluorocarbons.

Although all ultrasound contrast agents investigated to date such as free gas bubbles or encapsulated gas bubbles are potent backscatterers, these agents also have a high degree of attenuation. High attenuation leads to low imaging depth and loss of tissue images distal to the contrast agent. In many cases, the imaging information can be lost completely beyond regions having significant concentrations of the contrast agent, e.g. the left ventricle. All ultrasound contrast agents currently under investigation share this problem to some extent.

To minimize the problem associated with the attenuation of contrast agents, investigators have resorted to several approaches. Most frequently the amount of contrast agent administered is decreased to allow more of the ultrasound beam to penetrate through the contrast agent. Although the attenuation is lower, the decrease in dose leads to less than optimal contrast for many clinical indications. Alternatively, ultrasound contrast agents can be administered as a continuous infusion. This essentially lowers the local concentration of agent and has the problem described previously for dose reduction. Continuous infusion has the additional disadvantages of requiring a larger total dose over time and is not easy to perform in a clinical setting. To compensate for lower doses, investigators have used harmonic imaging to enhance the signal to noise ratio. However, harmonic imaging is not standard at this point in time.

Importantly, these approaches do not address rectifying the fundamental problem with the acoustic properties of existing ultrasound contrast agents. Thus for an ultrasound contrast agent to have high echogenicity it is necessary to create a scatterer which leads to high total returned power at the receiving transducer from regions of interest at depths beyond the initial region containing contrast agent. The returned power will be governed by both the backscatter and the attenuation of the agent.

It is therefore an object of the present invention to provide microparticles with significantly enhanced echogenicity. It is another object of the invention to provide an ultrasound agent with high backscatter and low attenuation.

SUMMARY OF THE INVENTION

It has been discovered that microparticles with thicker walls formed from natural or synthetic polymers have significantly enhanced echogenicity and lower attenuation as compared with microparticles having thinner walls. The effect of wall thickness has been determined theoretically and the optimum wall thicknesses predicted. Microparticles having these thicknesses were produced. In the preferred embodiment, the polymers are synthetic biodegradable polymers and the wall thickness is between 50 and 660 nm, although wall thicknesses from about 30 nm to in excess of 800 nm can be used. The shell thickness will depend on the target tissue to be imaged and will depend on both the blood volume and tissue volume of the target organ. The microparticles are manufactured with a diameter suitable for the targeted tissue to be imaged, for example, with a diameter of between 0.5 and 8 microns for intravascular administration, and a diameter of between 0.5 and 5 mm for oral administration for imaging of the gastrointestinal tract or other lumens. Preferred polymers are polyhydroxy acids such as polylactic acid-co-glycolic acid, polylactide polyglycolide or polylactide co-glycolide. These materials may be conjugated to polyethylene glycol or other materials inhibiting uptake by the reticuloendothelial system (RES). The microspheres may be used in a variety of ultrasound imaging applications including cardiology applications, blood perfusion applications as well as for organ and peripheral vein imaging.

BRIEF DESCRIPTION OF THE DRAWINGS

FIG. 1 is a graph of calculations of the effect of wall thickness on total scattering cross section per unit volume as a function of acoustic frequency for a representative size distribution of synthetic polymer microencapsulated octafluoropropane at a dilution of 1/1620 assuming wall thicknesses of 110 nm and 0.0034% $C_3F_8$ (total gas volume fraction), 165 nm and 0.0032% $C_3F_8$, 220 nm and 0.0029% $C_3F_8$, 330 nm and 0.0025% $C_3F_8$, 440 nm and 0.0021% $C_3F_8$, 660 nm and 0.0015% $C_3F_8$, 880 nm and 0.0010% $C_3F_8$, and 1100 nm and 0.0007% $C_3F_8$.

FIG. 2 is a graph of calculations of the effect of wall thickness on the acoustic attenuation coefficient as a function of acoustic frequency for a representative size distribution of synthetic polymer microencapsulated octafluoropropane at a dilution of 1/1620 assuming wall thicknesses of 110 nm and 0.0034% $C_3F_8$, 165 nm and 0.0032% $C_3F_8$, 220 nm and 0.0029% $C_3F_8$, 330 nm and 0.0025% $C_3F_8$, 440 nm and 0.0021% $C_3F_8$, 660 nm and 0.0015% $C_3F_8$, 880 nm and 0.0010% $C_3F_8$, and 1100 nm and 0.0007% $C_3F_8$.

FIG. 7 is a graph of calculations of the effect of wall thickness on echogenicity as a function of acoustic frequency for a representative size distribution of natural polymer microencapsulated air at a dilution of 1/5400 assuming wall thicknesses of 15 nm and 0.0006% air, 40 nm and 0.0006% air, 80 nm and 0.0006% air, 150 nm and 0.0006% air, and 300 nm and 0.0005% air.

DETAILED DESCRIPTION OF THE INVENTION

Figure 3:
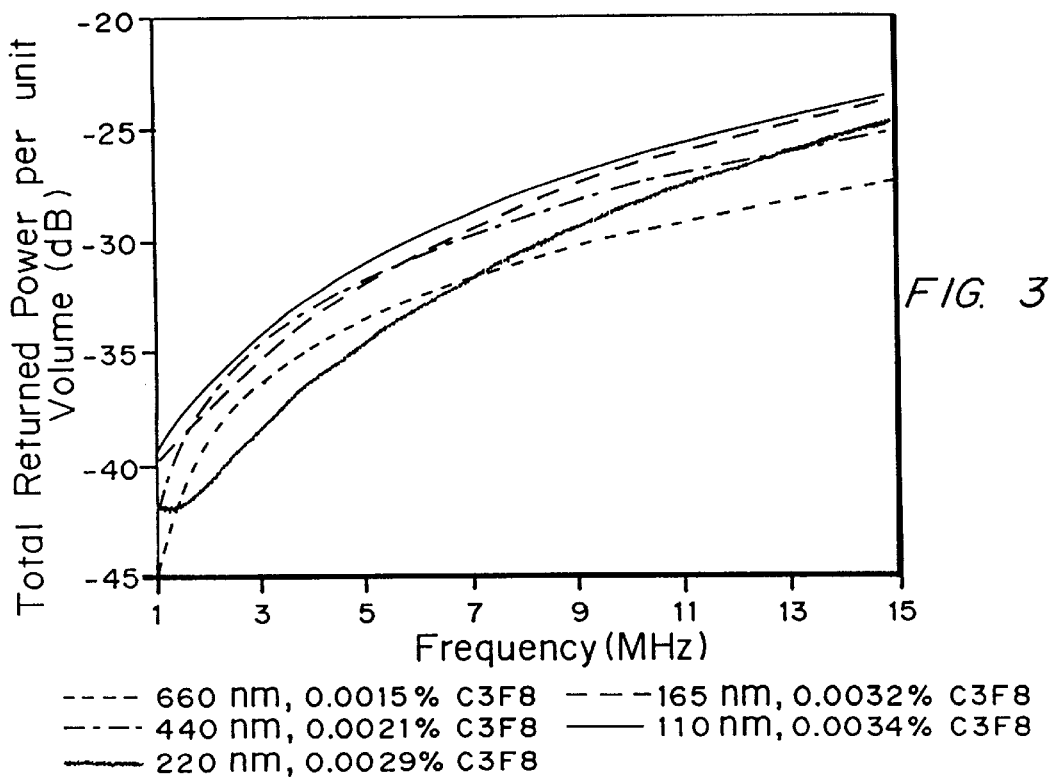
FIG. 3 is a graph of calculations of the effect of wall thickness on echogenicity (total returned power per unit volume) as a function of acoustic frequency for a representative size distribution of synthetic polymer microencapsulated octafluoropropane at a dilution of 1/1620 assuming wall thicknesses of 110 nm and 0.0034% $C_3F_8$, 165 nm and 0.0032% $C_3F_8$, 220 nm and 0.0029% $C_3F_8$, 440 nm and 0.0021% $C_3F_8$, and 660 nm and 0.0015% $C_3F_8$.

A method for maximizing echogenicity as a function of wall thickness of natural or synthetic polymeric microparticles is described. The microparticles are useful in a variety of diagnostic ultrasound imaging applications, particularly in ultrasound procedures such as blood vessel imaging and echocardiography. Increasing wall thickness significantly increases the echogenicity as compared with the same natural or synthetic polymeric microparticles with thinner walls.

I. Calculation of Optimal Polymer Thickness

In order to allow a greater understanding of the response of encapsulated microbubbles to diagnostic ultrasound, a mathematical model (C. Church *J. Acoustical Soc. Amer.* 97(3):1510–1521, 1995) was used to calculate important quantities such as backscatter and attenuation coefficients to the values of physical parameters such as the thickness and rigidity of the encapsulating shell. The shell can be either a natural or synthetic material. The model consists of a (nonlinear) Rayleigh-Plesset-like equation for the case of a spherical gas bubble encapsulated by a shell which behaves collectively as a continuous, incompressible, damped elastic solid. An analytical solution to this equation, which includes the lowest-order first and second harmonic components, is used here to estimate the effect of shell thickness on the scattering cross section (the ratio of the power scattered by the encapsulated gas bubbles to the intensity of the incident acoustic beam) and attenuation coefficient (the rate at which the gas bubbles remove acoustic energy from the beam) of a suspension of encapsulated gas bubbles. These quantifiers are then used to estimate the total returned power from a suspension of encapsulated gas bubbles to the ultrasound transducer emitting the incident pulse.

The Rayleigh-Plesset-like equation describing the response of an encapsulated gas bubble to an incident acoustic pressure wave is:

$$R_1 U_1 \left[1 + \left(\frac{\rho_L - \rho_S}{\rho_S}\right)\frac{R_1}{R_2}\right] + U_1^2\left[\frac{3}{2} + \left(\frac{\rho_L - \rho_S}{\rho_S}\right)\left(\frac{4R_2^3 - R_1^3}{2R_2^3}\right)\frac{R_1}{R_2}\right] = \quad (1)$$

$$\frac{1}{\rho_S}\left[P_{G,eq}\left(\frac{R_{ol}}{R_1}\right)^{3K} - P_\infty(t) - \frac{2\sigma_1}{R_1} - \right.$$

$$\left. \frac{2\sigma_2}{R_2} - \frac{4U_1}{R_1}\left(\frac{V_S\mu_S + R_1^3\mu_L}{R_2^3}\right) - \frac{4V_S G_S}{R_2^3}\left(1 - \frac{R_{e1}}{R_1}\right)\right]$$

where $R_1$ is the radius of the gas-filled cavity, $U_1$ is the radial velocity of interface 1 (the interface between the gaseous interior and the encapsulating solid), $R_2$ is the exterior radius of the encapsulating material, $P_S$ is the density of the liquid surrounding the bubble, $\rho_L$ is the density of the encapsulating shell, $P_{Gg,eg}$ is the equilibrium gas pressure within the bubble, $R_{01}$ is the initial radius of the gas-filled cavity, $P_\infty(t)$ is the pressure at infinity (including the acoustic driving pressure), $\sigma_1$ and $\sigma_2$ are the interfacial tensions at the gas-shell and shell-liquid interfaces, respectively, $\mu_S$ and $\mu_L$ are the effective viscosities of the shell and the surrounding liquid, respectively, $V_S = R_2^3 - R_1^3$, $G_S$ is the rigidity of the shell and $R_{e1}$ is the unstrained equilibrium position of the gas-shell interface. An expression for the scattering cross section $\sigma_{S1}$, of an encapsulated gas bubble may be found by assuming that the pulsation amplitude $R_{01}x(t)$ is small and substituting $R_1 = R_{01}(1+x)$ and related expressions into equation (1) of Church (1995). The resulting equation (2) is:

$$\sigma_{S_I}(R_{ol}) = \frac{4\pi R_{ol}^2 \varpi^4 \rho_L^2}{\rho_S^2 \left[1 + \left(\frac{\rho_L - \rho_S}{\rho_S}\right)\frac{R_{ol}}{R_{02}}\right]^2 [(\varpi_0^2 - \varpi^2)^2 + \delta_d^2 \varpi^2]} \quad (\text{cm}^2) \quad (2)$$

where $\overline{\omega}$ is the (radial) frequency of the incident acoustic wave, $\overline{\omega}_o$ is the resonance frequency of the encapsulated gas bubble and $\delta_d$ is the damping constant of the encapsulated gas bubble; representative units for cross section are given in the parenthetical following the equation.

Equation (2) is appropriate for cases in which the response of a single encapsulated gas bubble is of interest. In diagnostic ultrasound, it is more usual to be interested in the responses of a suspension of many millions of encapsulated gas bubbles. When a collection of encapsulated gas bubbles with a range of sizes is present, the total scattering cross section per unit volume may be estimated by simply summing the contribution from each encapsulated gas bubble in a representative volume of the suspension:

$$\sigma_{S\text{tot}}/\text{vol} = \int_0^\infty \sigma_{S_I}(R_{01}) f(R_{01}) dR_{01} \quad (\text{cm}^2/\text{cm}^3) \quad (3)$$

where $f(R_{01})dR_{01}$ is the number of encapsulated gas bubble per unit volume with radii between $R_{01}$ and $R_{01}+dR_{01}$. The attenuation coefficient of the suspension may be estimated using the method given by K. W. Commander and A. Prosperetti, "Linear pressure waves in bubbly liquids: Comparison between theory and experiments," *J. Acoust. Soc. Amer.* 85(2): 732–746 (1989). By describing a bubbly medium in terms of its average pressure, density, velocity, etc., these authors derived an expression for $C_m$, the complex speed of sound in the suspension. For the case of encapsulated gas bubbles, $$A = 8.686\left(\frac{\varpi v}{c}\right) \quad (\text{dB/cm}) \quad (4)$$

where the factor 8.686 is necessary to convert from neper to dB. Equations (3) and (4) may be combined to yield the following relationship for returned power:

$$P = I_o \sigma_{S\text{tot}}/\text{vol}\, G\exp\left(-\frac{4A}{8.686}x\right) = \quad (5)$$

$$I_o \sigma_{S\text{tot}}/\text{vol}\, G\exp\left(-\frac{4\varpi v}{c}x\right) \quad (\text{W}/\text{cm}^3)$$

where x is now the distance between the transducer and the sample volume, and the factor G accounts for additional geometrical factors including the transducer aperture, the distance between the transducer and the sample volume and the solid angle intercepted by the spherical wave scattered from each bubble at the receiving transducer.

In order to make use of these results, it is necessary to provide an encapsulated gas bubble size distribution and to estimate values for the physical parameters used in the model. Two cases are considered. The first is for synthetic microparticles produced from polyesters and the second is for microparticles produced from albumin. The size distribution for the synthetic particles used here is that measured for PLGA-PEG microparticles produced by spray drying, as described in U.S. Ser. No. 08/681,710 filed Jul. 29, 1996, now U.S. Pat. No. 5,837,221, the teachings of which are incorporated herein. The values of the population parameters characterizing this distribution, as determined by Coulter Multisizer® analysis are: total concentration: 2.4× $10^9$ particles/mL, number mean diameter: 2.2 $\mu$m, volume mean diameter: 4.6/$\mu$m and 6.5% gas volume fraction. The calculations given below were produced assuming a dilution of 1/1620. The corresponding concentration was 4.4×$10^6$ particles/mL while the gas volume fraction was approximately 0.01%. The values for the parameters used in the model are: internal gas: values appropriate for perfluoropropane, external liquid: values appropriate for water, shell density: 1.5 g/cm$^3$, shell viscosity: 30 poise, shell rigidity: 10 MPa and shell thicknesses: 22, 55, 110, 165, 220, 330, 440, 660, 880 and 1100 nm.

The results of calculations for the total scattering cross section at the driving frequency are shown in FIG. 1 for the range of PEG-PLGA shell thicknesses employed. At the lowest frequencies, the cross sections increase approximately as the fourth power of the frequency, as is expected for small, i.e., Rayleigh, scatterers. At higher, biomedical, frequencies, the total scattering increases only as frequency to the power 1.5. At still higher frequencies, scattering strength plateaus and then declines. The effect of increasing shell thickness is to decrease the total scattering cross section by an amount approximately equal to or somewhat greater than the proportional change in thickness. Thus the total scattering cross section exhibited by a suspension of encapsulated gas bubbles may be controlled by varying the shell thickness.

The results of calculations for the attenuation coefficient as a function of the driving frequency at different shell thicknesses are shown in FIG. 2. The effect of increasing shell thickness is to decrease the attenuation coefficient by an amount approximately equal to or somewhat less than the proportional change in thickness. Thus the attenuation coefficient may be controlled by varying the shell thickness.

The fact that both the total scattering cross section and the attenuation coefficient increase approximately in proportion to the decrease in shell thickness might seem to indicate the variation in shell thickness would have no effect on the total power expected to be backscattered to a transducer emitting an acoustic wave into a suspension of encapsulated gas bubbles. Upon further consideration from equation 5, however, it is apparent that suspensions of encapsulated gas bubbles possessing thicker shells will exhibit greater total returned power. This is shown in FIG. 3. The reason for this is that while total backscattered power is directly proportional to total scattering cross section, it is also proportional to the exponential of the attenuation coefficient. Therefore, if the shell thickness is decreased by a factor of two the effect of the increase in total scattering cross section will be to increase the total power by approximately two while the effect of attenuation will be to "increase" the total power by a factor of approximately $\exp(-2)=1/7.4$, for a net decrease of approximately 73%. Total returned power is increased as the shell thickness is increased.

Figure 4:
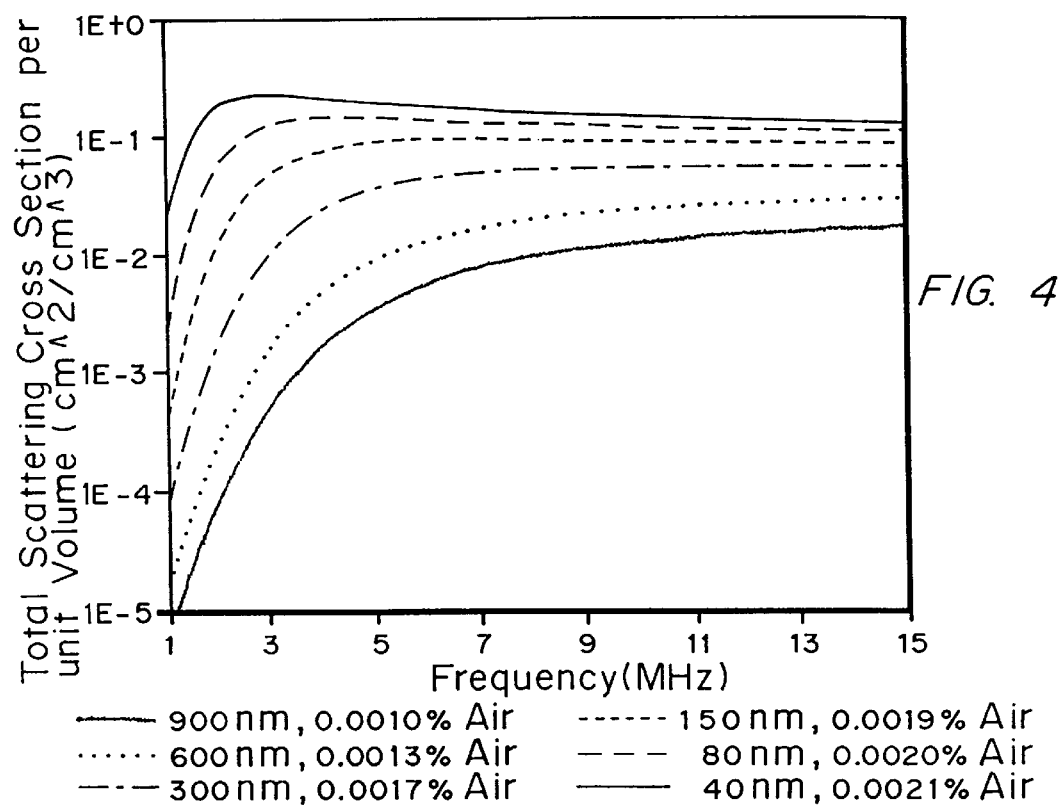
FIG. 4 is a graph of calculations of the effect of wall thickness on total scattering cross section per unit volume as a function of acoustic frequency for a representative size distribution of natural polymer microencapsulated air at a dilution of 1/1620 assuming wall thicknesses of 40 nm and 0.0021% air (total gas volume fraction), 80 nm and 0.0020% air, 150 nm and 0.0019% air, 300 nm and 0.0017% air, 600 nm and 0.0013% air, and 900 nm and 0.0010% air.
Figure 5:
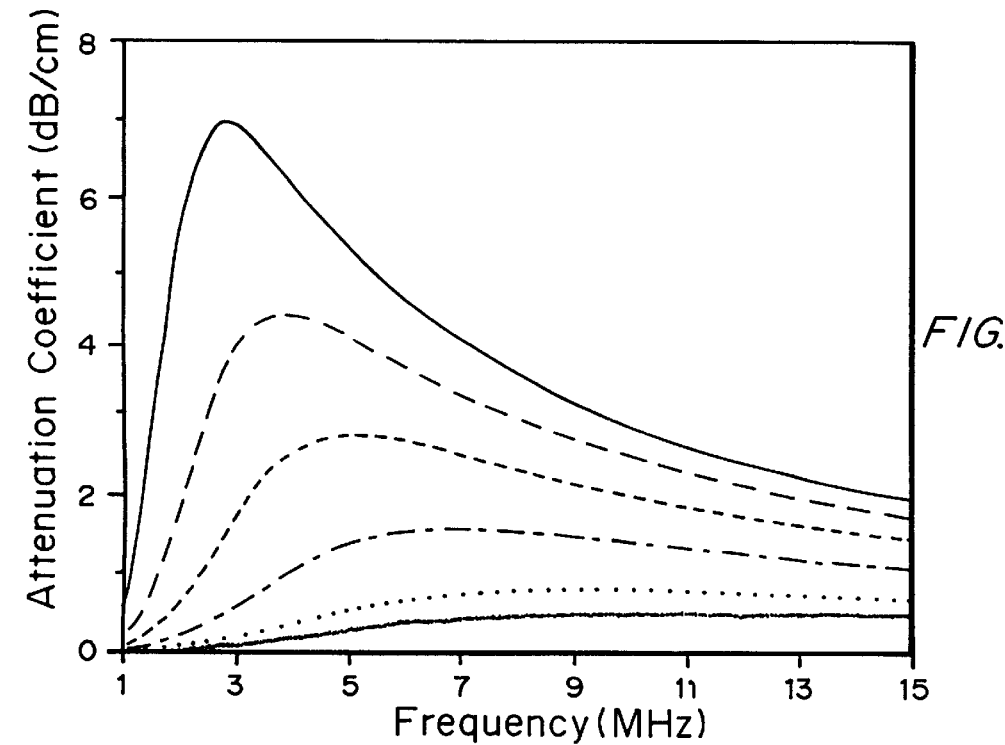
FIG. 5 is a graph of calculations of the effect of wall thickness on acoustic attenuation coefficient as a function of acoustic frequency for a representative size distribution of natural polymer microencapsulated air at a dilution of 1/1620 assuming wall thicknesses of 40 nm and 0.0021% air, 80 nm and 0.0020% air, 150 nm and 0.0019% air, 300 nm and 0.0017% air, 600 nm and 0.0013% air, and 900 nm and 0.0010% air.
Figure 6:
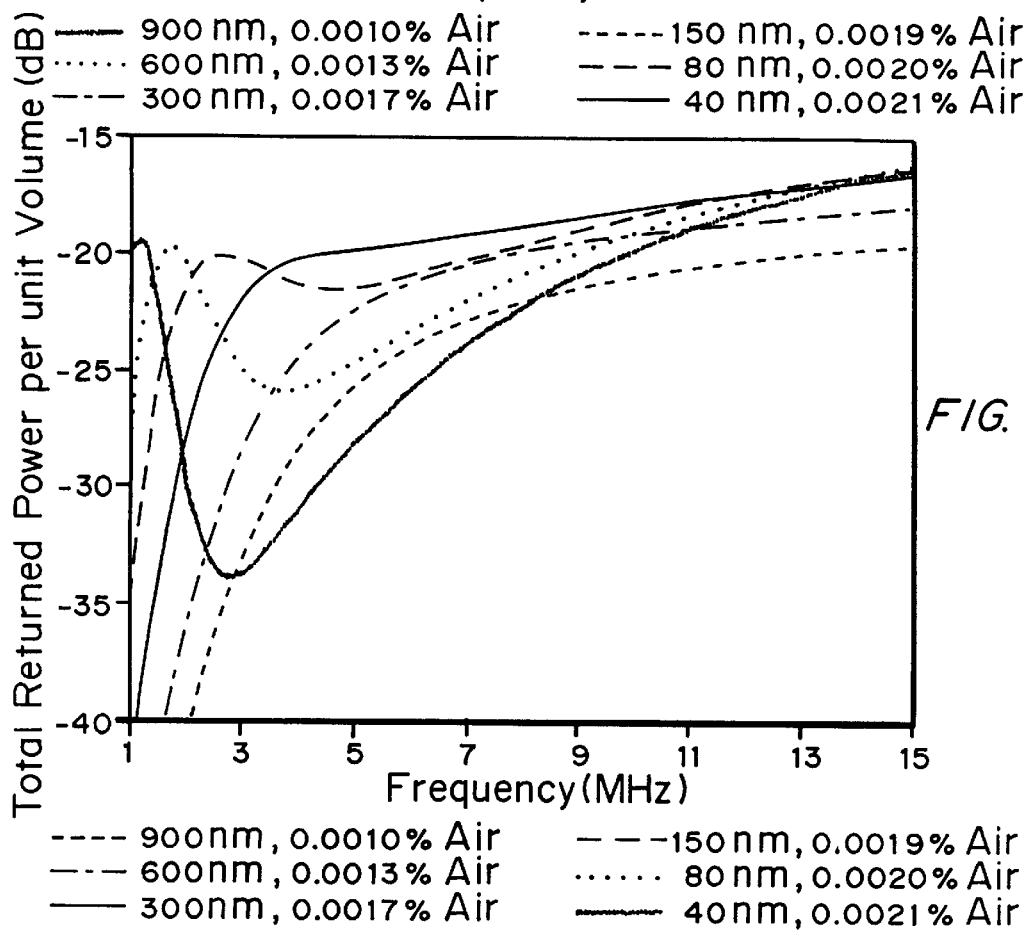
FIG. 6 is a graph of calculations of the effect of wall thickness on echogenicity (total returned power per unit volume) as a function of acoustic frequency for a representative size distribution of natural polymer microencapsulated air at a dilution of 1/1620 assuming wall thicknesses of 40 nm and 0.0021% air, 80 nm and 0.0020% air, 150 nm and .0019% air, 300 nm and 0.0017% air, 600 nm and 0.0013% air, and 900 nm and 0.0010% air.

Similar results are predicted for microparticles produced from albumin as shown in FIGS. 4–6. The parameters used for albumin are as disclosed in C. Church, *J. Acoustical Soc. Amer.*, 97(3):1510–1521 (1995).

The total returned power for the synthetic polymer microparticles (FIG. 3) and for the albumin microparticles (FIG. 6) are for a microparticle dilution factor of 1/1620. The optimal shell thickness (defined as that thickness providing a maximum in total returned power at a depth of 2 cm into a suspension of encapsulated gas bubbles) will depend on the dilution of encapsulated gas bubbles (i.e. concentration of encapsulated gas bubbles). This is shown in FIG. 7 for albumin microparticles at a dilution of 1/5400. As the suspension is diluted, it is possible to utilize microparticles with thinner shells. This occurs because although thinner shells lead to greater attenuation and greater scattering strength on a "per bubble" basis, this is offset sufficiently by the number of microparticles to yield higher total returned power.

The optimal shell thicknesses for three dilutions are summarized in the following table for both albumin and PEG-PLGA microparticles.

|  | Optimal Shell Thickness (nm) | |
| --- | --- | --- |
| Dilution | Albumin Microparticles | PEG-PLGA Microparticles |
| 1/540 | 300–600 | 660 |
| 1/1620 | 150–300 | 220 |
| 1/5400 | 40–80 | 55–110 |

For bubbles whose size distribution is relatively stable in vivo, the choice of optimal shell thickness would be based on the expected particle concentration in the target organ of interest. To illustrate how a shell thickness may be selected, the synthetic microparticles previously described are considered. If the microparticles are dosed at approximately 0.25 mL/kg and the blood volume is assumed to be 50 mL/kg, the microparticles would be diluted to 1/200 post intravenous injection. In the myocardium, the blood constitutes 10% of the total compartment volume and the microparticles are further diluted in the compartment by a factor of 10. Thus the final dilution would be approximately 1/2000. At this dilution, the optimal shell thickness may be extrapolated from the data in the table and is 200 nm. Thus the optimal thickness for use as a myocardial perfusion agent for these types of microparticles is approximately 200 nm.

Based on this information, thicker shells should be utilized to optimize the design of a particular microparticle encapsulating gas, minimizing attenuation and maximizing returned backscattered power, allowing high doses of ultrasound contrast agents to be utilized with minimal attenuation. Methods for producing microparticles with the appropriate wall thickness are disclosed.

II. Processes and Reagents for Making Microparticles with Different Shell Thicknesses As used herein, the term microparticle includes microspheres and microcapsules, as well as microparticles, unless otherwise specified. Microparticles may or may not be spherical in shape. Microcapsules are defined as microparticles having an outer polymer shell surrounding a core of another material, in this case, a gas. Microspheres are microparticles having a honeycombed structure formed by pores through the polymer or combinations of honeycombed or microcapsular structures which are filled with a gas for imaging purposes, as described below. The term "wall thickness" or "polymer thickness" refers to the diameter of the polymer from the interior of the microparticle to the exterior. In the case of a microcapsule with a hollow core, the wall thickness will be equal to the polymer thickness. In the case of porous microparticle having channels or pores in a polymer sphere, the wall thickness may be equal to one-half the diameter of the microparticle.

Polymers

Both non-biodegradable and biodegradable matrices can be used for the microencapsulation of gases, although biodegradable matrices are preferred, particularly for intravenous injection. Non-erodible polymers may be used for enterally administered ultrasound applications. Synthetic or natural polymers can be used to fabricate the microparticles. Synthetic polymers are preferred due to more reproducible synthesis and controlled degradation. The polymer is selected based on the time required for in vivo stability, in other words, that time required for distribution to the site where imaging is desired, and the time required for imaging.

Representative synthetic polymers are: poly(hydroxy acids) such as poly(lactic acid), poly(glycolic acid), and poly(lactic acid-co-glycolic acid), polyglycolides, polylactides, polylactide co-glycolide copolymers and blends, polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate) (jointly referred to herein as "polyacrylic acids"), poly(butyric acid), poly (valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred non-biodegradable polymers include ethylene vinyl acetate, poly(meth)acrylic acid, polyamides, copolymers and mixtures thereof.

Examples of preferred biodegradable polymers include polymers of hydroxy acids such as lactic acid and glycolic acid, polylactide, polyglycolide, polylactide-co-glycolide, and copolymers with PEG, polyanhydrides, poly(ortho) esters, polyurethanes, poly(butyric acid), poly(valeric acid), poly(lactide-co-caprolactone), blends and copolymers thereof.

Examples of preferred natural polymers include proteins such as albumin, hemoglobin, fibrinogen, polyamino acids, gelatin, lactoglobulin and prolamines, for example, zein, and polysaccharides such as alginate, cellulose and polyhydroxyalkanoates, for example, polyhydroxybutyrate. Proteins can be stabilized by crosslinng with an agent such as glutaraldehyde or heat denaturation.

Bioadhesive polymers of particular interest for use in imaging of mucosal surfaces, as in the gastrointestinal tract, include polyanhydrides, polyacrylic acid, poly(methyl methacrylates), poly(ethyl methacrylates), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Solvents

As defined herein, the polymer solvent is an solvent that is volatile or has a relatively low boiling point or can be removed under vacuum and which is acceptable for administration to humans in trace amounts, such as methylene chloride, water, ethyl acetate, ethanol, methanol, dimethyl formamide (DMF), acetone, acetonitrile, tetrahydrofuran (THF), acetic acid, and dimethyl sulfoxide (DMSO), or combinations thereof. In general, the polymer is dissolved in the solvent to form a polymer solution having a concentration of between 0.1 and 60% weight to volume (w/v), more preferably between 0.25 and 30%.

Gases

Any biocompatible or pharmacologically acceptable gas can be incorporated into the microparticles. The term gas refers to any compound which is a gas or capable of forming a gas at the temperature at which imaging is being performed. The gas may be composed of a single compound such as oxygen, nitrogen, xenon, argon, nitrogen, fluorinated gases, or a mixture of compounds such as air. Fluorinated gases are preferred. Examples of fluorinated gases include $CF_4$, $C_2F_6$, $C_3F_8$, $C_4F_8$, $SF_6$, $C_2F_4$, and $C_3F_6$. Perfluoropropane is particularly preferred because it is pharmacologically acceptable. Typically, hollow air filled microparticles are produced by the methods disclosed and the air within the microparticles can be exchanged with any of the biocompatible gases disclosed. The gas is typically exchanged by pulling a vacuum on the microparticles to remove the air and then applying an atmosphere of the biocompatible gas at a particular temperature and pressure. The temperature and pressure of the gas to be exchanged will depend on the properties of the microparticles.

Pore Forming Agents

Pore forming agents may be microencapsulated to introduce internal voids. The pore forming agent may be a liquid or a volatile or sublimable salt which may be removed during the microencapsulation or may be removed after the microparticles are formed by using vacuum drying or lyophllization. After the removal of the pore forming agent, internal voids are created which can be filled with the gas of interest. More than one pore forming agent may be used. The pore forming agent or agents can be included in the polymer solution in an amount of between 0.01% and 90% weight to volume, to increase pore formation. For example, in spray drying, solvent evaporation, a pore forming agent such as a volatile salt, for example, ammonium bicarbonate, ammonium acetate, ammonium chloride or ammonium benzoate or other lyophilizable salt can be encapsulated as solid particles or as a solution. If the pore forming agent is encapsulated as a solution, the solution containing the pore forming agent is emulsified with the polymer solution to create droplets of the pore forming agent in the polymer. The polymer solution containing the particles of the pore forming agent or the emulsion of the pore forming agent solution in the polymer is then spray dried or taken through a solvent evaporation/extraction process. After the polymer is precipitated, the hardened microparticles may be frozen and lyophilized to remove the residual pore forming agent or the hardened microparticles may be vacuum dried to remove the pore forming agent.

Additives to Stabilize Encapsulated Gas Lipids

In general, incorporation of compounds during the production of the microparticles which are hydrophobic and, in an effective amount, thereby limit penetration and/or uptake of water by the microparticles, is effective in stabilizing the echogenicity of polymeric microparticles having gas encapsulated therein, especially fluorinated gases such as perfluorocarbons. Lipids which may be used to stabilize gas inside the polymeric microparticles include but are not limited to the following classes of lipids: fatty acids and derivatives, mono-, di and triglycerides, phospholipids, sphingolipids, cholesterol and steroid derivatives, terpenes and vitamins. Fatty acids and derivatives thereof may include but are not limited to saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include, but are not limited to, molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauric, physeteric, myristoleic, palmitoleic, petroselinic, and oleic acids. Examples of branched fatty acids that may be used include, but are not limited to, isolauric, isomyristic, isopalmitic, and isostearic acids and isoprenoids. Fatty acid derivatives include 12-(((7'-diethylaminocoumarin-3 yl)carbonyl)methylamino)-octadecanoic acid; N-[12-(((7'diethylaminocoumarin-3-yl) carbonyl)methyl-amino) octadecanoyl]-2-aminopalmitic acid, N-succinyl-dioleoylphosphatidylethanol amine and palmitoyl-homocysteine; and/or combinations thereof. Mono, di and triglycerides or derivatives thereof that may be used include, but are not limited to molecules that have fatty acids or mixtures of fatty acids between 6 and 24 carbon atoms, digalactosyldiglyceride, 1,2-dioleoyl-sn-glycerol;1, 2-dipalmitoyl-sn-3 succinylglycerol; and 1,3-dipalmitoyl-2-succinylglycerol.

Phospholipids which may be used include but are not limited to phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-allyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

Sphingolipids which may be used include ceramides, sphingomyelins, cerebrosides, gangliosides, sulfatides and lysosulfatides. Examples of Sphinglolipids include, but are not limited to, the gangliosides GM1 and GM2.

Steroids which may be used include but are not limited to cholesterol, cholesterol sulfate, cholesterol hemisuccinate, 6-(5-cholesterol 3β-yloxy) hexyl-6-amino-6-deoxyl-1-thio-α-D-galactopyranoside, 6-(5-cholesten-3β-tloxy)hexyl-6-amino-6-deoxyl-1-thio-α-D mannopyranoside and cholesteryl)4'-trimethyl 35 ammonio)butanoate.

Additional lipid compounds which may be used include tocopherol and derivatives, and oils and derivatized oils such as stearlyamine.

A variety of cationic lipids such as DOTMA, N-[1-(2,3-dioleoyloxy)propyl-N,N,N-trimethylammonium chloride; DOTAP, 1,2-dioleoyloxy-3-(trimethylammonio) propane; and DOTB, 1,2-dioleoyl-3-(4'-trimethyl-ammonio) butanoyl-sn glycerol may be used.

The most preferred lipids are phospholipids, preferably DPPC, DAPC, DSPC, DTPC, DBPC, DLPC and most preferably DPPC, DAPC and DBPC.

The lipid content ranges from 0.01–30 (w lipid/w polymer); most preferably between 0.1–12 (w lipid/w polymer). The lipids may be added to the polymer solution prior to the formation of the microparticles.

Other Hydrophobic Compounds

Other preferred hydrophobic compounds include amino acids such as tryptophane, tyrosine, isoleucine, leucine, and valine, aromatic compounds such as an alkyl paraben, for example, methyl paraben, and benzoic acid.

Microparticles and Methods for Manufacture Thereof

In the most preferred embodiment, the microparticles are produced by spray drying. The polymer and the pore forming agent are atomized through a nozzle and the polymer solvent is evaporated off by a heated drying gas. Other techniques can be used, such as solvent extraction, hot melt encapsulation, and solvent evaporation, to produce microparticles having a wall thickness of the appropriate diameter to optimize echogenicity. Pore forming agents are typically used to create the internal voids. The pore forming agents are microencapsulated and removed after the microparticle formation by lyophilization or vacuum drying. Solvent evaporation is described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984). Hot-melt microencapsulation is described by E. Mathiowitz, et al., *Reactive Polymers*, 6, 275 (1987).

A variety of surfactants may be added during the synthesis of the microparticles. Exemplary emulsifiers or surfactants which may be used (0.1–5% by weight) include most physiologically acceptable emulsifiers. Examples include natural and synthetic forms of bile salts or bile acids, both conjugated with amino acids and unconjugated such as taurodeoxycholate, and cholic acid.

Microparticle Size

In a preferred embodiment for the preparation of injectable microparticles capable of passing through the pulmonary capillary bed, the microparticles should have a diameter of between approximately one and ten microns. Larger microparticles may clog the pulmonary bed, and smaller microparticles may not provide sufficient echogenicity. Larger microparticles are useful for administration by routes other than injection, for example oral (for evaluation of the gastrointestinal tract), application to other mucosal surfaces (rectal, vaginal, oral, nasal) or by inhalation. The preferred particle size for oral administration is between about 0.5 microns and 5 mm. Particle size analysis can be performed on a Coulter counter, by light microscopy, scanning electron microscopy, or transmittance electron microscopy.

Control of Wall Thickness

The preferred wall thickness is greater than 20 nm, more preferably in the range of between 160 and 220 nm up to about 700 nm, at which point the advantage derived by increasing the wall thickness begins to taper off. For each of the microencapsulation techniques previously described, there are several ways in which the fmal shell thickness of the polymer microparticle can be controlled.

Polymer Concentration

The final thickness of the polymer shell can be increased by increasing the concentration of the polymer phase during the encapsulation process. This is applicable to synthetic polymers or natural polymers such as proteins or polysaccharides. For a given polymer droplet size, using a more concentrated polymer solution will result in more polymer per unit volume of droplet and thus a thicker shell. The concentration of polymer to achieve a given shell thickness will depend primarily on the polymer type, the polymer solvent, the solubility of the polymer in solvent system and, the temperature at which the encapsulation is conducted. Polymer concentrations in the range of between 0.1 and 60% can be used. Preferred polymer concentrations are in the range of between 0.5 and 30%.

As previously described, pore forming agents such as volatile or sublimable salts can be utilized to produce microparticles with internal voids.

The pore forming agent may be microencapsulated as solids or as an aqueous solution or can be codissolved in the polymer solution. For the case of solid pore forming agents, the size of the solid particles and the amount of the solid agent encapsulated will govern the final polymer shell thickness. Thinner microparticles shells will result as the diameter of the solid pore forming particles is increased relative to the polymer droplet phase or as the weight of solid pore forming agent relative to polymer droplet phase is increased. The diameter of the solid pore forming microparticles is between 1 and 95% of the diameter of the polymer droplet phase. The diameter of the solid pore forming agent can be adjusted to the appropriate diameter using standard techniques such as jet milling. The weight of solid pore forming agent to be encapsulated is between one and 50% (w/w polymer).

For the case of a pore forming agent which is dissolved in the polymer solvent, the shell concentration will be governed by the amount of pore forming agent encapsulated. As the total amount of pore forming agent is increased, the final shell thickness will decrease.

For a pore forming agent microencapsulated as an aqueous solution, the final polymer shell thickness will be governed by the volume of pore forming solution encapsulated relative to the polymer phase, the weight of pore forming agent microencapsulated and the droplet size of the pore forming agent solution relative to the polymer droplet size. The final polymer shell thickness will decrease as the volume ratio of the pore forming solution is increased relative to the polymer phase. The volume ratio of pore forming solution relative to polymer phase is between 0.002 and 0.5 with preferred ratios in the 0.01 to 0.1 range. For a given volume ratio of pore forming agent, the polymer shell thickness will decrease as the concentration of the pore forming agent in the pore forming solution to be encapsulated is increased. The weight of pore forming agent to be encapsulated is between one and 50% (w/w polymer). As the droplet size of the pore forming solution to be encapsulated relative to the polymer solution is decreased, the shell thickness of the final microparticle will increase. The droplet size of the pore forming solution can be controlled by the process used to create the droplets. The diameter of the pore forming solution droplets is in the range of between one and 95% of the diameter of the polymer droplet phase. If homogenization is used to create the pore forming droplets, the speed of homogenization (500–20,000 rpm), the time of homogenization (0.1–10 minutes), the temperature of homogenization (4–50° C.) and the type of blade (i.e. slotted head, square head, circular head) used will all govern the final pore forming solution droplet size. The homogenization conditions are adjusted to create the droplet size of interest. If sonication is utilized to create the droplets of the liquid pore forming solution in the polymer droplet, the sonication probe type, the time of sonication (0.1–10 minutes), the temperature of sonication (4–40° C.), the probe frequency and the sonication power can all be used to alter the droplet size.

III. Diagnostic Applications

Microparticles are typically combined with a pharmaceutically acceptable carrier such as phosphate buffered saline or saline or mannitol, then an effective amount for detection administered to a patient using an appropriate route, typically by injection into a blood vessel (i.v.) or orally. Microparticles containing an encapsulated imaging agent may be used in vascular imaging, as well as in applications to detect liver and renal diseases, in cardiology applications, in detecting and characterizing tumor masses and tissues, and in measuring peripheral blood velocity. The microparticles also can be linked with ligands that minimize tissue adhesion or that target the microparticles to specific regions of the body in vivo as described above.

The methods and compositions described above will be further understood with reference to the following non-limiting examples.

EXAMPLE 1

Production of Polymeric Microparticles having Enhanced Echogenicity 3.2 grams of PEG-PLGA (75:25) (IV=0.75 dL/g), 6.4 g PLGA (50:50) (IV=0.4 dL/g), and 384 mg diarachidoylphosphatidylcholine were dissolved in 480 ml of methylene chloride. 20 ml of a 0.18 g/ml Ammonium Bicarbonate solution was added to the polymer solution and the polymer/salt mixture was homogenized at 10,000 RPM for 2 minutes using a Virtis homogenizer. The solution was pumped at a flowrate of 20 ml/min and sprayed dried using a Buchi Lab spray dryer. The inlet temperature was 40° C. and the outlet temperature was 20–22° C. The particle diameters ranged from 1–10 microns when sized on a coulter counter with a number average mean of 2.0 microns. Scanning electron microscopy demonstrated the particles to be generally spherical with smooth surfaces and occasional surface crenulations. The microspheres were prepared for transmission electron microscopy by embedding in LR white resin followed by polymerization under UV light. Thin sections were cut on a LKB ultramicrotome using a glass knife and viewed on a Zeiss EM-10 TEM at 60 kv. The shell thickness of the microparticles are in the range of between 200 and 240 nm.

Modifications and variations will be apparent to those skilled in the art from the foregoing detailed description. Such modifications and variations are intended to come within the scope of the following claims.

We claim:

1. A method for increasing the echogenicity of microparticles encapsulating a gas for use in ultrasound imaging comprising determining the range of wall thicknesses of the microparticles resulting in the highest amounts of total returned power as a function of the material forming the microparticles and the gas to be encapsulated, and producing microparticles with a wall thickness in the range resulting in the highest levels of total returned power.

2. The method of claim 1 wherein the microparticles are formed of a synthetic polymer.

3. The method of claim 2 wherein the wall thickness of the microparticles is between 50 and 660 nm.

4. The method of claim 1 wherein the microparticles are formed of a natural polymer.

5. The method of claim 4 wherein the natural polymer is a protein and the wall thickness of the microparticles is between 20 to 600 nm.

6. A method of ultrasound imaging comprising administering to a subject to be imaged a composition of polymeric microparticles encapsulating a gas, wherein the microparticles are formed of non-proteinaceous polymer, and consist essentially of a subpopulation of microparticles selected from a population of microparticles having a broader range of wall thicknesses between 110 and 1100 nm, wherein the echogenicity of the subpopulation of microparticles is greater than the echogenicity of the population of microparticles from which the subpopulation is derived.

7. The method of claim 6 wherein the microparticles are formed of a synthetic polymer.

8. The method of claim 7 wherein the wall thickness of the population of microparticles is between 110 and 660 nm.

9. The method of claim 6 wherein the microparticles are formed of a natural polymer.

10. A method of ultrasound imaging comprising administering to a subject to be imaged a composition of polymeric microparticles encapsulating a gas, wherein the microparticles are formed of protein and the microparticles consist essentially of a subpopulation of microparticles selected from a population of microparticles having a broader range of wall thicknesses between 20 and 600 nm. wherein the echogenicity of the subpopulation of microparticles is greater than the echogenicity of the population of microparticles from which the subpopulation is derived.

11. The method of claim 6 wherein the gas is a fluorinated gas.

12. An ultrasound composition comprising polymeric microparticles encapsulating an echogenic amount of a biocompatible gas, wherein the microparticles consist essentially of a subpopulation of microparticles selected from a population of microparticles having a wall thickness of between 110 and 1100 nm based on polymer wall thickness wherein the echogenicity of the subpopulation of microparticles is greater than the echogenicity of the population from which the subpopulation is derived.

13. The composition of claim 12 wherein the polymer is a synthetic polymer other than a block copolymer of polyethyleneglycol and poly(lactide-co-glycolide).

14. The composition of claim 12 wherein the polymeric microparticles are formed of a polymer selected from the group consisting of poly(hydroxy acids), polyanhydrides, polyorthoesters, polyamides, polycarbonates, polyalkyienes, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes, synthetic celluloses, polyacrylic acids, poly(butyric acid), poly(valeric acid), and poly(lactide-co-caprolactone), polysaccharides, polyhydroxyalkanoates, copolymers and blends thereof.

15. The composition of claim 12 wherein the gas is selected from the group consisting of oxygen, nitrogen, xenon, argon, nitrogen, fluorinated gases, and air.

16. The composition of claim 15 wherein the gas is a fluorinated gas selected from the group consisting of $CF_4$, $C_2F_6$, $C_3F_8$, C4F8, $SF_6$, $C_2F_4$, and $C_3F_6$.

17. The composition of claim 14, wherein the population of microparticles have a wall thickness of between 110 nm and 330 nm.

18. The method of claim 6 further comprising determining the dilution of the microparticles at which echogenicity is greatest.

19. The method of claim 10 wherein the gas is a fluorinated gas.

* * * * *